US006500934B1

(12) United States Patent
Lerner et al.

(10) Patent No.: US 6,500,934 B1
(45) Date of Patent: *Dec. 31, 2002

(54) BIVALENT AGONISTS FOR G-PROTEIN COUPLED RECEPTORS

(76) Inventors: Michael Rush Lerner, 280 W. Renner Rd., #2112, Richardson, TX (US) 75080; Michael D. Carrithers, 216 Bishop St., Apt. 309, New Haven, CT (US) 06511

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 282 days.

(21) Appl. No.: 08/686,934

(22) Filed: Jul. 24, 1996

(51) Int. Cl.$^7$ .......................... C07K 7/00; C07K 14/68; C07K 14/705
(52) U.S. Cl. ................... 530/402; 530/300; 530/312; 530/350; 530/306; 514/2; 514/12; 435/7.2; 435/7.21
(58) Field of Search ................ 530/300, 312, 530/350, 402, 306, 399, 326, 327; 514/2, 12; 435/7.2, 7.21

(56) References Cited

FOREIGN PATENT DOCUMENTS

WO    WO 9323550    * 11/1993

OTHER PUBLICATIONS

Costa et al., Dimeric pentapeptide enkephalin: a novel prove of delta opiate receptors, Life Sci., 31(15): 1625–32, Nov. 1982.*
Portoghese et al., Stereostructural–activity relationship of opiod agonists and antagonist bivalent ligands, J. Med. Chem., 28(9): 1140–1, Sep. 1995.*
Carrithers and Lerner, 1996, "Synthesis and characterization of bivalent peptide ligands targeted to G–protein–coupled receptors", Chemistry and Biology 3:1–6.
Cascieri et al., 1995, "Molecular characterization of a common binding site for small molecules within the transmembrane domain of G–protein coupled receptors", J. Pharmacological and Toxicological Methods 33:179–185.
Conn et al., 1982, "Potency enhancement of a GnRH agonist: GnRH–receptor microaggregation stimulates gonadotropin release", Endocrinology 111:335–337.
Conn et al., 1982, "Conversion of a gonadotropin–releasing hormone antagonist to an agonist", Nature 296:653–655.
Crothers and Metzger, 1972, "The influence of polyvalency on the binding properties of antibodies", Immunochemistry 9:341–357.
Delisi and Crothers, 1971, "Theory of the influence of oligonucleotide chain conformation on doucble helix stability", Biopolymers 10:1809–1927.
Duncan et al., 1994, "Polymer conjugates", Clin. Pharmacokinet 27:290–306.

Engel et al., 1991, "Designed coiled–coil proteins: synthesis and spectroscopy of two 78–residue α–helical dimers", Biochem. 30:3161–3169.
Fuh et al., 1992, "Rational design of potent antagonists to the human growth hormone receptor", Science 256:1677–1680.
Graminski et al., 1993, "Pigment dispersion in frog melanophores can be induced by a phorbol ester or stimulation of a recombinant receptor that activates phospholipase C", J. Biol. Chem. 268:5957–5964.
Holliger et al., 1993, "Diabodies: small bivalent and bispecific antibody fragments", Proc. Natl. Acad. Sci. USA 90:6444–6448.
Jayawickreme et al., 1994, "Discovery and structure–function analysis of α–melanocyte–stimulating hormone antagonists", J. Biol. Chem. 269:29846–29854.
Jayawickreme et al., 1994, "Creation and functional screening of a multi–use peptide library", Proc. Natl. Acad. Sci. USA 91: 1614–1618.
Karne et al., 1993, "Cloning and characterization of an endothelin–3 specific receptor ($ET_c$ Receptor) from *Xenopus laevis* dermal melanophores", J. Biol. Chem. 268:19126–19133.
Laerum et al., 1988, "The dimer of hemoregulatory peptide (HP5B) stimulates mouse and human myelopoiesis in vitro", Exp. Hematol. 16:274–280.
Laerum et al., 1987, "A synthetic hemoregulatory peptide (HP5B) inhibits human myelopoietic colony formation (CFU–GM) but not leukocyte phagocytosis in vitro", Eur. J. Haematol. 39:259–266.
Lee et al., 1984, "New synthetic cluster ligands for galactose/N–acetylgalactosamine–specific lectin of mammalian liver", Biochemistry 23:4255–4261.
Maggio et al., 1993, "Coexpression studies with mutant muscarinic/adrenergic receptors provide evidence for intermolecular 'cross talk' between G–protein–linked receptors", Proc. Natl. Acad. Sci. USA 90:3103–3107.

(List continued on next page.)

*Primary Examiner*—Claire M. Kaufman
(74) *Attorney, Agent, or Firm*—Pennie & Edmonds LLP

(57) ABSTRACT

Bivalent agonists having affinity for one or more G-protein coupled receptors, comprising two agonist or two antagonist ligand domains, wherein the distance between the ligand domains can range from about 40 to about 250 Å, and further comprising a backbone, wherein the backbone is covalently bonded to the two ligand domains, are provided. Additionally, bivalent agonists are provided that comprise one agonist and one antagonist ligand domain. In a specific embodiment, the bivalent agonists are peptide dimers, wherein the backbone comprises two spacer regions, two polylysine regions, and a disulfide bond region, such that the order in which the ligand domains, spacer regions, polylysine regions and disulfide bond region are covalently bonded together is: (ligand domain)-(spacer region)-(polylysine region)-(disulfide bond region)-(polylysine region)-(spacer region)-(ligand domain). Such peptide dimers are prepared from oxidative dimerization of their corresponding monomers.

55 Claims, 4 Drawing Sheets

OTHER PUBLICATIONS

Mallender et al., 1994, "Construction, expression, and activity of a bivalent bispecific single–chain antibody", J. Biological Chemistry 269:199–206.

Neri et al., 1995, "High–affinity antigen binding by chelating recombinat antibodies (CRAbs)", J. Mol. Biol. 246:367–373.

Pack et al., 1992, "Miniantibodies: use of amphipathic helices to produce functional, flexibly linked dimeric $F_v$ fragments with high avidity in *Escherichia coli*", Biochemistry 31:1579–1584.

Page et al., 1971, "Entropic contributions to rate accelerations in enzymic and intramolecular reactions and the chelate effect", Proc. Natl. Acad. Sci USA 68:1678–1683.

Paukovits et al., 1990, "Homoregulatory peptide pGlu–Glu–Asp–Cys–Lys: a new synthetic derivative for avoiding dimerization and loss of inhibitory activity", Molecular Pharmacology 38:401–409.

Plank et al., 1994, "The influence of endosome–disruptive peptides on gene transfer using synthetic virus–like gene transfer systems", J. Biol. Chem. 269:12918–12924.

Potenza et al., 1992, "A Method for evaluating the effects of ligands upon $G_s$ protein–coupled receptors using a recombinant melanophore–based bioassay", Anal. Biochem. 206:315–322.

Quillan et al., 1995, "Combinatorial diffusion assay used to identify topically active melanocyte–stimulating hormone receptor antagonists", Proc. Natl. Acad. Sci USA 92:2894–2898.

Schertler et al., 1993, "Projection structure of rhodopsin", Nature 362:770–772.

Seed, 1994, "Making agonists of antagonists", Chemistry and Biology 1:125–129.

Slate et al., 1995, "Engineering of five 88–residue receptor–adhesive modular proteins containing a parallel α–helical coiled coil and two RGD ligand sites", Int. J. Peptide Protein Res. 45:290–298.

Spike et al., 1952, "Thermodynamics of chelation. I. The statistical factor in chelate ring formation", J. Amer. Chem. Soc. 75: 2726–2729.

Strader et al., 1994, "Structure and function of G protein–coupled receptors", Annul. Rev. Biochem. 63:101–132.

Strader et al., 1995, "The family of G–protein–coupled receptors", FASEB J. 9:745–754.

Tam et al., 1991, "Disulfide bond formation in peptides by dimethyl sulfoxide. Scope and applications", J. Am. Chem. Soc. 113:6657–6662.

Bagutti C et al. 1994. [111In]–DTPA–labeled analogues of alpha –melanocyte–stimulating hormone for melanoma targeting:receptor binding in vitro and in vivo. Int J Cancer. 58(5):749–55.

Celis ME et al. 1976. Release of melanocyte–stimulating hormone by neurohypophyseal hormone fragments. Monograph. pp. 771–6.

Gawlek et al. 1991. Homodimeric forms of bombesin act as potent antagonists of bombesin on Swiss 3T3 cells. Growth Factors. 5(2):159–70.

Lackie PM et al. 1985 Localisation of receptors using a dimeric ligand and electron immunocytochemistry. Histochemistry. 83(1):57–9.

\* cited by examiner

US 6,500,934 B1

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 13 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:1:

Ser Tyr Ser Met Glu His Phe Arg Trp Gly Lys Pro Val
1              5                      10

(2) INFORMATION FOR SEQ ID NO:2:

(i) SEQUENCE CHARACTERISTICS:
        (A) LENGTH: 14 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:2:

Met Leu His Gly Val Ala Trp Gln Asn Gly Leu Arg Gln Gln
1              5                      10

(2) INFORMATION FOR SEQ ID NO:3:

(i) SEQUENCE CHARACTERISTICS:
        (A) LENGTH: 38 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 17
        (D) OTHER INFORMATION: /note="Xaa denotes n-aminohexanoic acid"
        (A) NAME/KEY: Modified Site

```
            (B) LOCATION: 38
            (D) OTHER INFORMATION: /note="Xaa denotes a-alanine"

(xi) SEQUENCE DESCRIPTION: SEQ ID NO:3:

Ser Tyr Ser Met Glu His Phe Arg Trp Gly Lys Pro Val Gly Gly Gly
1               5                   10                  15

Xaa Lys Lys Lys Lys Lys Lys Lys Lys Lys Lys Lys Lys Lys Lys Lys
            20                  25                  30

Lys Lys Lys Lys Lys Xaa
            35

(2) INFORMATION FOR SEQ ID NO:4:

(i) SEQUENCE CHARACTERISTICS:
            (A) LENGTH: 38 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified Site
            (B) LOCATION: 21
            (D) OTHER INFORMATION: /note="Xaa denotes n-aminohexanoic
                acid"

(xi) SEQUENCE DESCRIPTION: SEQ ID NO:4:

Lys Lys Lys Lys Lys Lys Lys Lys Lys Lys Lys Lys Lys Lys Lys
1               5                   10                  15

Lys Lys Lys Lys Xaa Gly Gly Gly Gln Gln Arg Leu Gly Asn Gln Trp
            20                  25                  30

Ala Val Gly His Leu Met
            35
```

BIVALENT AGONISTS FOR G-PROTEIN COUPLED RECEPTORS

This invention was made with government support under grant no. N00014-91-J-1920 awarded by The Office of Naval Research. The government has certain rights in the invention.

1. FIELD OF THE INVENTION

The present invention relates to bivalent agonists having affinity for GPCRs, peptide dimers useful as bivalent agonists, and methods for their preparation and use.

2. BACKGROUND OF THE INVENTION

G-Protein coupled receptors ("GPCRs") are plasma membrane proteins capable of transducing signals across a cell membrane so as to initiate a second messenger response. To this end, GPCRs bind a variety of ligands ranging from small biogenic amines to peptides, small proteins and large glycoproteins (C. D. Strader et al., *Annu. Rev. Biochem.* 63, 101–132 (1994)). All GPCRs contain seven hydrophobic domains, which have been postulated to span the plasma membrane, connected by hydrophilic extracellular and intracellular loops. Some examples of GPCR subfamilies include the rhodopsin/β-androgenic ("βAR") family, which includes receptors for dopamine, serotonin, substance P, bradykinin, angiotensin, somatostatin and lutropin; the secretin/vasointestinal peptide ("VIP") family, which includes receptors for secretin, glucagon, glucagon-like peptide 1, gastric inhibitory peptide, parathyroid hormone, secretin/vasointestinal peptide, pituitary adenylate cyclase activating peptide, calcitonin and growth releasing hormone; and the metabotropic glutamate ("mGlu") family, which includes receptors for glutamate. Over 250 GPCRs have been identified to date (M. A. Cascieri et al., *JPM* 33(4), 179–185 (1995); C. D. Strader et al., *FASEB J.* 9, 745–754 (1995)), including $Ca^{2+}$, olefactory, prostaglandin and sweet-taste receptors.

Multivalent ligands such as immunoglobulins have significantly enhanced affinity for their binding site. Based on the entropic effects of avidity, multivalency theoretically can increase apparent binding affinity by several orders of magnitude (D. M. Crothers et al., *Immunochemistry* 9, 341–357 (1972)). Although this affinity gain is usually more modest, multivalent molecules have potentially powerful applications in clinical pharmacology. For example, synthetic bivalent ligands can be used to target toxins, drugs and, potentially, plasmid DNA to specific cell subtypes, or across the blood-brain barrier.

Thermodynamically, the binding of a multivalent antibody to adjacent epitopes on the cell surface is similar to the chelate effect (C. G. Spike et al., *J. Amer. Che. Soc.* 75, 2726–2729 (1953); D. Neri et al.,*J. Mol. Biol.* 246, 367–373 (1995)). Although this effect was described originally to explain the enhanced stability of chelate rings, it is also relevant in rate accelerations of enzymatic reactions and in base pair formation of polynucleotides (M. I. Page et al., *Proc. Natl. Acad. Sci. USA* 68, 1678–1683 (1971); C. Delisi et al., *Biopolymers* 10, 1809–1827 (1971)). The common feature of these reactions is that following the initial reaction (e.g., binding of one antibody "arm" to its antigen), each succeeding reaction (e.g., binding of the second antibody "arm" to an adjacent epitope) is more favorable because the entropy loss is decreased.

Specific examples of bivalent molecules capable of binding to adjacent epitopes include small bivalent antibodies composed of either antibody fragments ($F_{ab}$) or single chain antibodies ($F_v$) (P. Pack et al., *Biochemistry* 31, 1579–1584 (1992); P. Holliger et al., *Proc. Natl. Acad. Sci. USA* 90, 6444–6448 (1993); W. D. Mallender et al., *J. Biol. Chem.* 269, 199–206 (1994)). In addition, other multivalent molecules have been designed to bind to adjacent epitopes, including bivalent carbohydrates and a variety of synthetic drug delivery systems (R. T. Lee et al., *Biochemistry* 23, 4255–4261 (1984); R. Duncan et al., *Clin. Pharmacokinet.* 27, 290–306 (1994)).

Bivalent peptides, such as receptor-adhesive modular proteins ("RAMPs"), have been used in an alternative approach to cell targeting (M. Engel et al., *Biochemistry* 30, 3161–3169 (1991); C. A. Slate et al., *Int. J. Peptide Protein Res.* 45, 290–298 (1995)). These large synthetic peptides, which contain two ligand sites separated by a spacer region and a dimerization domain, were designed with the hope of binding to two membrane receptors simultaneously. In its original design, the dimerization domain consisted of a two stranded parallel alpha helical coiled coil, and the ligand region was composed of two identical integrin receptor binding peptides. However, although the two ligand domains were separated by at least 50 angstroms, no increased affinity of their dimeric constructs was demonstrated, suggesting that such dimeric peptides could not bind to two receptors at the same time. Previous studies suggested that the minimal distance between two GPCRs is 40 angstroms (Å) (G. F. X. Schertler et al., *Nature* 362, 770–772 (1993)), while structural studies of immunoglobins have demonstrated that the distance between antigen binding sites is 100–250 Å (D. M. Crothers et al., *Immunochemistry* 9, 341–357 (1972)).

Previous studies indicated that short, crosslinked gonadotropin releasing hormone ("GnRH") peptide dimers that were incubated with anti-GnRH antibodies to form larger dimers having a bridge length of 150 Å, increased agonist activity, relative to their corresponding short dimers, in a functional luteinizing hormone ("LH") release assay (P. M. Conn et al., *Endocrinology* 111, 335–337 (1982)).

In addition, it has been shown that a reversible association of an antibody with two GnRH antagonists resulted in the association having agonistic activity (P. M. Conn et al., *Nature* 296, 653–654 (1982)). However, in that case, because there was no covalent or ionic bonding between the two GnRH antagonists and the antibody, such an reversible association is easily disrupted, leading to cessation of agonist activity.

It has been speculated that a dimer of any small molecule that binds to a single transmembrane receptor that is known to work through dimerization, with an appropriate spacer portion to allow mutual contact of the active moieties with their receptors, could possibly possess agonist activity (B. Seed, *Chemistry & Biology* 1(3), 125–29 (1994)).

There is a clear need in the art for easily synthesizable agonists with enhanced functional activity or in vivo efficacy than those currently available.

Citation or identification of any reference in Section 2 of this application shall not be construed as an admission that such reference is available as prior art to the present invention.

3. SUMMARY OF THE INVENTION

The present invention provides a bivalent agonist having affinity for one or more G-protein coupled receptors, said agonist comprising two ligand domains, the ligand domains being agonists for a first and a second G-protein coupled receptor, respectively, wherein the distance between the ligand domains ranges from about 40 to about 250 Å, and further comprising a molecular backbone, said backbone being covalently bonded to the two ligand domains.

The invention further provides a bivalent agonist having affinity for one or more G-protein coupled receptors, said agonist comprising two ligand domains, the ligand domains being antagonists for a first and a second G-protein coupled receptor, respectively, wherein the distance between the ligand domains ranges from about 40 to about 250 Å, and further comprising a molecular backbone, said backbone being covalently bonded to the two ligand domains.

The invention further provides a bivalent agonist having affinity for one or more G-protein coupled receptors, said agonist comprising a first and second ligand domain, the first ligand domain being an agonist for a first G-protein coupled receptor, and the second ligand domain being an antagonist for a second G-protein coupled receptor, wherein the distance between the ligand domains ranges from about 40 to about 250 Å, and further comprising a molecular backbone, said backbone being covalently bonded to the first and second ligand domains.

The invention further provides a method for synthesizing a bivalent agonist dimer, comprising the step of treating an amount of a monomer with an amount of an oxidizing agent, the monomer comprising a ligand domain covalently bonded to a molecular backbone, said ligand domain (a) being an agonist for a G-protein coupled receptor, and (b) comprising a peptide; the backbone comprising a spacer region, a polylysine region, and an amino acid residue containing a sulfhydryl group in covalent linkage; said amount of oxidizing agent being capable of oxidizing the sulfhydryl group, such that an oxidized sulfhydryl group reacts with an unoxidized sulfhydryl group of another monomer so as to form a dimer having a disulfide bond.

The invention further provides a method for synthesizing a bivalent agonist dimer, comprising the step of treating an amount of a monomer with an amount of an oxidizing agent, the monomer comprising a ligand domain covalently bonded to a molecular backbone, said ligand domain (a) being an antagonist for a G-protein coupled receptor, and (b) comprising a peptide; the backbone comprising a spacer region, a polylysine region, and an amino acid residue containing a sulfhydryl group in covalent linkage; said amount of oxidizing agent being capable of oxidizing the sulfhydryl group, such that an oxidized sulfhydryl group reacts with an unoxidized sulfhydryl group of another monomer so as to form a dimer having a disulfide bond.

The invention still further provides a method for agonizing one or more G-protein coupled receptors expressed by a cell, comprising contacting a cell with a bivalent agonist, said agonist comprising two ligand domains, the ligand domains being agonists for a first and a second G-protein coupled receptor, respectively, wherein the distance between the ligand domains ranges from about 40 to about 250 Å, said agonist further comprising a molecular backbone, said backbone being covalently bonded to the two ligand domains.

The invention still further provides a method for agonizing one or more G-protein coupled receptors expressed by a cell, comprising contacting a cell with a bivalent agonist, said agonist comprising two ligand domains, the ligand domains being antagonists for a first and a second G-protein coupled receptor, respectively, wherein the distance between the ligand domains ranges from about 40 to about 250 Å, said agonist further comprising a molecular backbone, said backbone being covalently bonded to the two ligand domains.

The invention still further provides a method for agonizing one or more G-protein coupled receptors expressed by a cell, comprising contacting a cell with a bivalent agonist, said agonist comprising a first and second ligand domain, the first ligand domain being an agonist for a first G-protein coupled receptor, and the second ligand domain being an antagonist for a second G-protein coupled receptor, wherein the distance between the ligand domains ranges from about 40 to about 250 Å, said agonist further comprising a molecular backbone, said backbone being covalently bonded to the first and second ligand domains.

Further still, the invention provides a composition for agonizing one or more G-protein coupled receptors comprising a bivalent agonist having affinity for one or more G-protein coupled receptors, said agonist comprising two ligand domains, the ligand domains being agonists for a first and a second G-protein coupled receptor, respectively, wherein the distance between the ligand domains ranges from about 40 to about 250 Å, and further comprising a molecular backbone, said backbone being covalently bonded to the two ligand domains, the amount of said bivalent agonist being effective for agonizing one or more G-protein coupled receptors; and a pharmaceutically acceptable carrier.

Further still, the invention provides a composition for agonizing one or more G-protein coupled receptors comprising a bivalent agonist having affinity for one or more G-protein coupled receptors, said agonist comprising two ligand domains, the ligand domains being antagonists for a first and a second G-protein coupled receptor, respectively, wherein the distance between the ligand domains ranges from about 40 to about 250 Å, and further comprising a molecular backbone, said backbone being covalently bonded to the two ligand domains, the amount of said bivalent agonist being effective for agonizing one or more G-protein coupled receptors; and a pharmaceutically acceptable carrier.

Further still, the invention provides a composition for agonizing one or more G-protein coupled receptors comprising a bivalent agonist having affinity for one or more G-protein coupled receptors, said agonist comprising a first and second ligand domain, the first ligand domain being an agonist for a first G-protein coupled receptor, and the second ligand domain being an antagonist for a second G-protein coupled receptor, wherein the distance between the ligand domains ranges from about 40 to about 250 Å, and further comprising a molecular backbone, said backbone being covalently bonded to the first and second ligand domains, the amount of said bivalent agonist being effective for agonizing one or more G-protein coupled receptors; and a pharmaceutically acceptable carrier.

3.1 Abbreviations

| | |
|---|---|
| A | alanine |
| βAla | β-alanine |
| C | cysteine |
| E | glutamic acid |
| F | phenylalanine |
| G | glycine |
| H | histidine |
| K | lysine |
| L | leucine |
| M | methionine |
| N | asparagine |
| P | proline |

-continued

| | |
|---|---|
| Q | glutamine |
| R | arginine |
| S | serine |
| V | valine |
| W | tryptophan |
| Y | tyrosine |
| ε-Ahx | ε-aminohexanoic acid |
| α-MSH | α-melanocyte stimulating hormone |
| α-MSH-ANT | α-melanocyte stimulating hormone receptor antagonist |
| Boc | tert-butyloxycarbonyl |
| DIEA | N,N-diisopropylethylamine |
| DMF | N,N-dimethylformamide |
| DMSO | dimethyl sulfoxide |
| $EC_{50}$ | concentration at which 50% of the agonist response is achieved |
| Fmoc | 9-fluorenylmethoxycarbonyl |
| GnRH | gonadotropin releasing hormone |
| GPCR | G-protein coupled receptor |
| HBTU | 2-(1H-benzotriazol-1-yl)-1,1,3,3-tetramethyl uronium hexafluorophosphate |
| HOBt | 1-hydroxybenzotriazole |
| HPLC | high pressure liquid chromatography |
| $IC_{50}$ | concentration at which 50% of the antagonist response is achieved |
| MBHA | methylbenzhydrylamine |
| NMP | N-methylpyrrolidinone |
| PBS | phosphate buffered saline |
| PI | phosphatidylinositol |
| Pmc | 2,2,5,7,8-pentamethylchroman-6-sulfonyl |
| tBu | tert-butyl |
| TFA | trifluoroacetic acid |
| Trt | trityl |

It is to be understood that when the designation "d" immediately precedes a letter abbreviation for an amino acid as defined above, that amino acid is the unnatural, d-enantiomer.

The present invention may be understood more fully by reference to the following figures, detailed description and illustrative examples which are intended to exemplify non-limiting embodiments of the invention.

4. DESCRIPTION OF THE FIGURES

Figure 4:
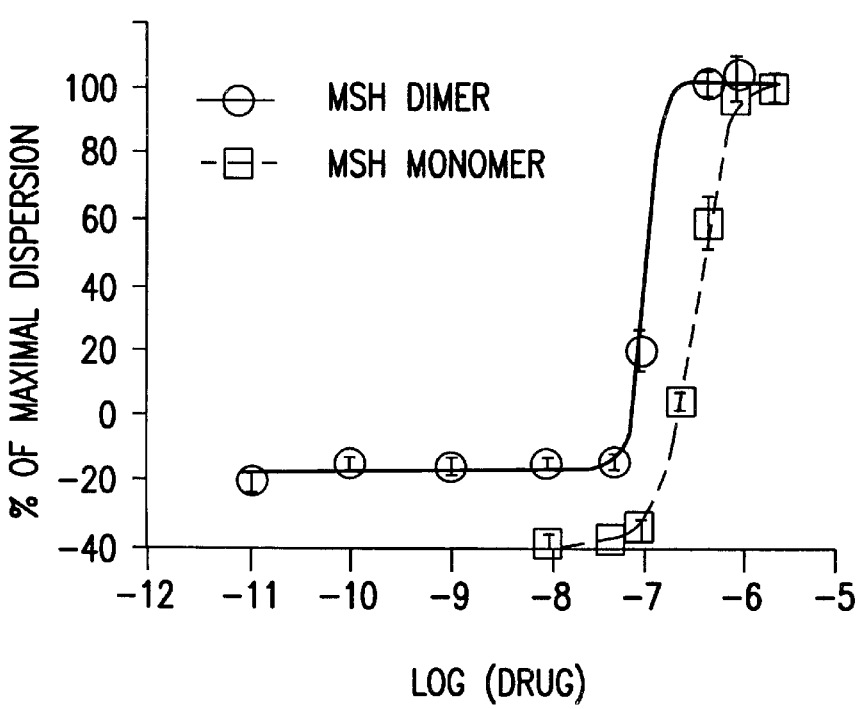

FIG. 4 is a graph showing the effect of α-MSH monomer and of α-MSH dimer on melanocyte pigment dispersion in a dose dependent manner. By "Drug" is meant α-MSH monomer or α-MSH dimer. Each point in the graph represents the mean from triplicate samples. ○=α-MSH dimer; □=α-MSH monomer.

Figure 5:
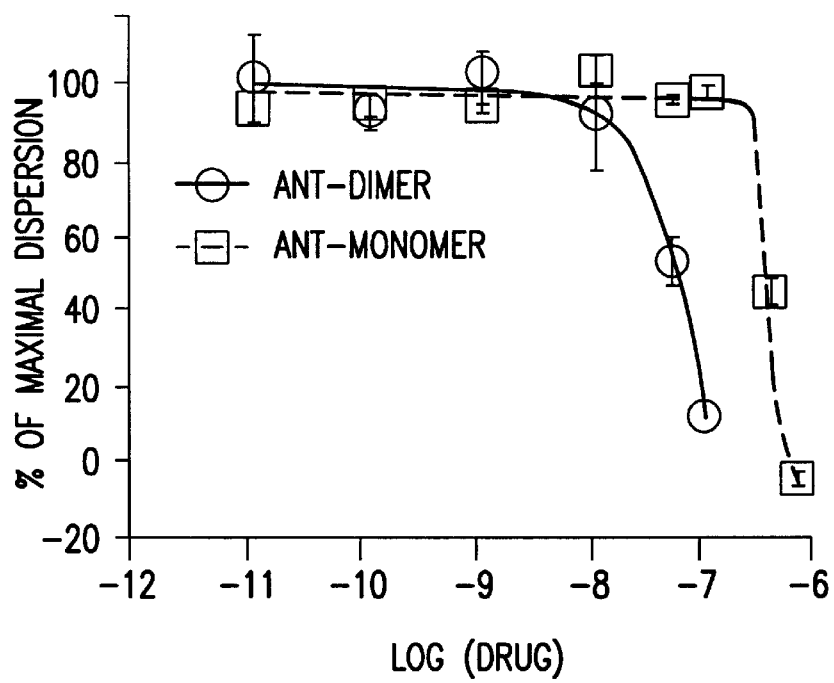

FIG. 5 is a graph showing the effect of α-MSH-ANT monomer and of α-MSH-ANT dimer on melanocyte pigment dispersion in a dose dependent manner. By "Drug" is meant α-MSH-ANT monomer or α-MSH-ANT dimer. Each point in the graph represents the mean from triplicate samples. ○=α-MSH-ANT dimer; □=α-MSH-ANT monomer.

Figure 6:
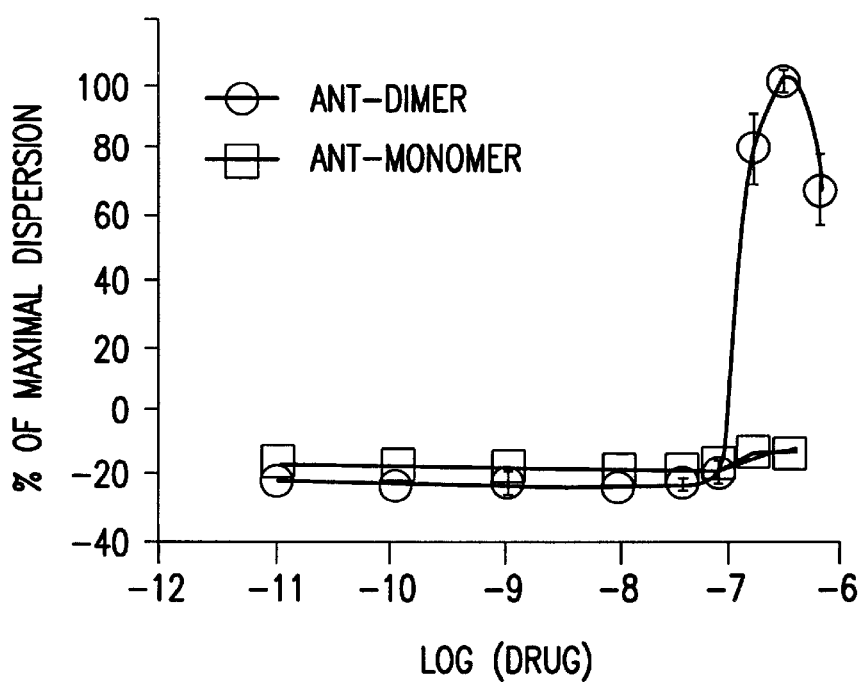

FIG. 6 is a graph showing the effect of monomeric and dimeric α-MSH-ANT on melanocyte pigment dispersion in a dose dependent manner. By "Drug" is meant α-MSH-ANT monomer or α-MSH-ANT dimer. Each point in the graph represents the mean from triplicate samples. ○=α-MSH-ANT dimer; □=α-MSH-ANT monomer.

Figure 7:
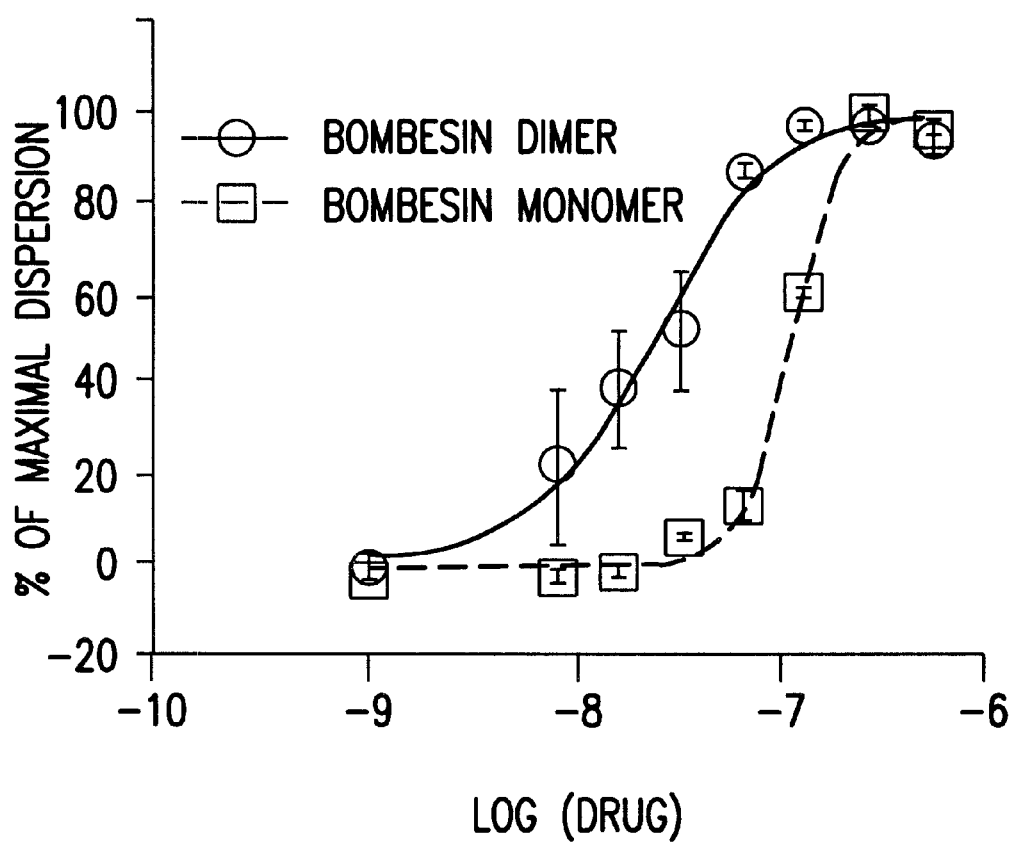

FIG. 7 is a graph showing the effect of monomeric and dimeric bombesin on melanocyte pigment dispersion in a dose dependent manner. By "Drug" is meant bombesin monomer or bombesin dimer. Each point in the graph represents the mean from triplicate samples. ○=bombesin dimer; □=bombesin monomer.

5. DETAILED DESCRIPTION OF THE INVENTION

5.1 Bivalent Agonists

The inventors have discovered that the present bivalent agonists have agonist activity toward GPCRs whether the bivalent agonists have two agonist ligand domains, two antagonist ligand domains, or one agonist ligand domain and one antagonist ligand domain. Where the bivalent agonists have two ligand domains which are by themselves agonists for the same or different GPCRs, the agonist activity of the bivalent agonist is surprisingly synergistically higher than that of the two individual agonist ligands. Where the bivalent agonists have two ligand domains which are by themselves antagonists, the activity of the bivalent agonist is surprisingly stimulatory, rather than antagonistic. Where the bivalent agonists have one agonist ligand domain and one antagonist ligand domain, the activity of the bivalent agonist is stimulatory. Since it is believed that the bivalent agonists of the invention are effective agonists at sufficiently lower amounts than previously reported agonists, use of the bivalent agonists of the invention should avoid toxicity problems associated with the use of agonist ligand domains.

The present invention provides bivalent agonists having affinity for GPCRs. By "bivalent" is meant that the agonists comprise two ligand domains, each having affinity for a GPCR. The GPCRs can be either the same or different. The ligand domains are molecular components (via covalent linkage) of the bivalent agonist of the present invention. Each ligand domain has specific binding affinity for a GPCR. It is to be understood that the ligand domains of the bivalent agonists of the present invention can be the same or different. In a preferred embodiment, one of the GPCRs to which one of the ligand domains has affinity, is an MSH-receptor. In another embodiment, both of the GPCRs to which the two ligand domains have affinity, are MSH-receptors.

The ligand domains facilitate binding between the bivalent agonists and GPCRs of a desired cell type. Useful ligand domains are independently selected from the group consisting of proteins (including peptides and polypeptides), or their derivatives, including, but not limited to, hormones, antigens, synthetic or naturally occurring drugs, and the like; opiates; dopamine; serotonin; $Ca^{2+}$; catecholamines; thrombin; acetylcholine; prostaglandins; small molecules such as fragrances; pheromones; adenosine; simple sugars such as sucrose, glucose, lactose and galactose; any other moieties that recognize and have affinity toward GPCRs; and mixtures thereof.

Particular compounds useful as agonist ligand domains include, but are not limited to, angiotensin II, bradykinin, N-formyl-Met-Leu-Phe (chemotactic peptide), dynorphyn A fragment 1-13, (D-Ser$^2$)-leucine enkephalin-Thr, bombesin, human growth hormone releasing factor, human LH-RH, α-MSH, kinetensin, neurotensin, morphiceptin, (Thr$^4$ , Gly$^7$)-oxytocin, somatostatin, (Sar$^9$,Met(O$_2$)$^{11}$-substance P, and natural ligands for the GPCR of interest.

Particular compounds useful as antagonist ligand domains include, but are not limited to, (Sar$^1$,Ala$^8$)-angiotensin II, (D-Phe$^7$)-bradykinin, N-t-Boc-Met-Leu-Phe (chemotactic peptide antagonist), N-carboxymethyl-Phe-Leu, leupeptin, N-acetyl-Pen-Arg-Gly-Asp-Cys, (D-Phe$^{12}$,Leu$^{14}$)-bombesin, (N-acetyl-Tyr$^1$,D-Arg$^2$ fragment 1-29 amide, (D-Phe$^2$, D-Ala$^6$)-LH-RH, (D-Trp$^{11}$)-neurotensin, vasopressin and (D-Arg$^1$,D-Trp$^{7,9}$,Leu$^{11}$)-substance P. Useful α-MSH antagonists include D-Trp-Arg-Xaa-NH$_2$, wherein Xaa is Leu, Nle, Nva, Met, D-Nle, Ile, Abu, Val, Arg or D-Arg; D-Trp-Xaa-Nle-NH$_2$, wherein X is Lys, D-Arg, Leu, Nle, Ala, Met or Abu; and Xaa-Arg-Nle-NH$_2$, wherein Xaa is D-Phe, D-Tyr, Ac-D-Trp, Trp and D-His (J. M. Quillan et al., *Proc. Natl. Acad. Sci. USA* 92, 2894–2898 (1995)).

Other compounds useful as agonist or antagonist ligand domains can be selected from among those known in the art, e.g., from among the agonists and antagonists disclosed in the Sigma Chemical Company's catalog of Biochemical, Organic Compounds and Diagnostic Reagents (1996), available from Sigma Chemical Co., St. Louis, Mo. The above-specified peptide agonists and antagonists, as well as other compounds useful as agonist or antagonist ligand domains can be obtained, e.g., from Sigma Chemical Co., St. Louis, Mo.; and from Peninsula Laboratories, Belmont, Calif. Alternatively, the above specific peptide agonists and antagonists, as well as other compounds useful as agonist or antagonist ligand domains can be synthesized, or purified from natural sources or from recombinant expression systems, by methods well known in the art.

It is to be pointed out that as used herein, an "agonist" is a molecule that activates a receptor specific for that molecule, so as to elicit an appropriate second messenger response in the signal transduction pathway of that receptor. Thus, the binding of an agonist to its receptor elicits a biological response mediated by the receptor. As used herein, "antagonist" is meant a compound that binds to a receptor such that the compound prevents an agonist from agonizing the receptor. Thus, the binding of an antagonist to the receptor does not elicit a biological response mediated by the receptor.

Examples of GPCRs include, but are not limited to, rhodopsin/β-adrenergic receptors, which include receptors for dopamine, serotonin substance P, bradykinin, angiotensin, somatostatin and lutropin; secretin/vasoactive intestinal peptide receptors, which include receptors for secretin, glucagon, glucagon-like peptide 1, gastric inhibitory peptide, parathyroid hormone secretin/vasoactive intestinal peptide pituitary adenylate cyclase activating peptide, calcitonin and growth releasing hormone; and Mglu receptors, which include receptors for glutamate. See C. D. Strader et al., *Annu. Rev. Biochem.* 63, 101–132 (1994)); M. A. Cascieri et al., *JPM* 33(4), 179–185 (1995); and C. D. Strader et al., *FASEB J.* 9, 745–754 (1995).

The two ligand domains of the bivalent agonists can either be both agonists, both antagonists, or one agonist and one antagonist.

In addition to the use of known agonists and antagonists, potential compounds for use as agonists or antagonists for GPCRs can be screened for their potential agonist or antagonist activity by any methods known in the art, such as, for example, contacting a cell type having GPCRs, known to elicit a particular physiological response, with the desired compound. If the particular physiological response is elicited, the compound is an agonist. By way of example, to assay for compounds having antagonist activity for the same G-protein coupled receptor, the cell type is contacted with a mixture of the compound known to be an agonist for the desired physiological response, and a compound potentially having antagonist activity. If the physiological response normally observed with the agonist is diminished in the presence of the compound potentially having antagonist activity, the latter compound is an agonist for that particular GPCR.

The bivalent agonists of the invention can either be monospecific or bispecific. By "monospecific" is meant that the two ligand domains, i.e., two agonist ligands, two antagonist ligands, or one agonist and one antagonist ligand, have selective binding affinity for one type of GPCR. In monospecific bivalent agonists, the two ligand domains are preferably identical. By "bispecific" (heterospecific) is meant that the two ligand domains, i.e., two agonist ligands, two antagonist ligands, or one agonist and one antagonist ligand, are non-identical and are selective for different types of GPCRs.

As stated above, the present invention encompasses bispecific bivalent agonists. For example, in a specific embodiment, one ligand domain of a bivalent agonist comprises α-MSH-ANT, while the other ligand domain comprises a bombesin antagonist. Regardless of the particular ligand domains selected for incorporation into the bivalent agonists of the invention, it is believed that bispecific dimeric antagonists have substantial agonist activity generally only on cells expressing both receptor types, and these target cells would specifically endocytose the bivalent agonist. For example, a bivalent agonist that comprised α-MSH-ANT as one ligand domain and a bombesin antagonist as the other domain would be endocytosed most efficiently by cells expressing both receptors and much less so by cells only expressing one or none of the two different receptors. On the other hand, in the case of bispecific bivalent agonists that have two ligand domains that by themselves are agonists, cells having GPCRs that are specific for one or both of the two bispecific ligand domains are believed capable of engulfing the bivalent agonist. Combined with the benefits of enhanced avidity, bispecific agonists that have ligand domains which by themselves act as antagonists could enhance uptake by targeted cells by up to an order of magnitude.

Therefore, in a preferred method of agonizing a cell of interest using a bispecific agonist of the invention, wherein the agonist comprises a first antagonist ligand domain which recognizes a first GPCR, and a second, different antagonist ligand domain which recognizes a second, different GPCR, the cell of interest expresses the first or the second GPCR, preferably both the first and second GPCR. Where the bispecific bivalent agonist comprises two agonist ligand domains, the cell of interest preferably expresses the first or the second GPCR, more preferably both the first and second GPCR. Where the bispecific bivalent agonist comprises one agonist which recognizes a first GPCR and one antagonist ligand domain which recognizes a second GPCR, the cell of interest preferably expresses at least the first GPCR, more preferably both the first and second GPCR. In a particularly preferred embodiment wherein a bispecific bivalent agonist comprising two agonist ligand domains is used, the two ligand domains bind to the same GPCR, and the cell expresses that GPCR.

Thus, the present invention provides a method for agonizing (activating so as to elicit an appropriate second messenger response) one or more GPCRs expressed by a cell, comprising contacting a cell with a bivalent agonist, the agonist comprising two ligand domains, the ligand domains being both agonists or both antagonists for a first and a second G-protein coupled receptor, respectively, wherein the distance between the ligand domains ranges from about 40 to about 250 Å, the agonist further comprising a molecular backbone, the backbone being covalently bonded to the two ligand domains.

In addition, the present invention provides a method for agonizing one or more GPCRs expressed by a cell, comprising contacting a cell with a bivalent agonist, said agonist comprising a first and a second ligand domain, the first ligand domain being an agonist for the first GPCR, and the second ligand domain being an antagonist for a second GPCR, wherein the distance between the ligand domains ranges from about 40 to about 250 Å, the agonist further comprising a molecular backbone, the backbone being covalently bonded to the two ligand domains.

In various embodiments of the methods for agonizing one or more GPCRs expressed by a cell, the cell can express either the first or the second GPCR (recognized by the two ligand domains, respectively), or the cell can express both the first and the second GPCRs. In addition, the GPCRs recognized by the ligand domains of the bivalent agonists of the present invention can be the same or different. In a specific embodiment, either the first or the second GPCR is an MSH-receptor. In a preferred embodiment, the first and the second GPCRs are MSH-receptors.

By "contacting" is meant allowing the bivalent agonists to come into close proximity to the cell such that the bivalent agonists can associate with the GPCR molecules of that cell. Such contacting can occur via oral or parenteral (including intramuscular, sub-cutaneous and intravenous) administration, as well as other modes of administration known in the art, to a human or veterinary patient, of the bivalent agonist of the invention, preferably in a composition further comprising a pharmaceutically acceptable vehicle or carrier (see Section 5.4), for treatment or amelioration of a disease or disorder by agonizing a GPCR.

The contacting can also be carried out in vitro, for example, as part of an assay for determining the potential pharmaceutical properties of various bivalent agonists of the invention, or for determining or studying potential physiological responses mediated by GPCRs.

The cell type that can be used can be a member of any class of cells that express particular GPCRs for which one, or preferably both, ligand domains of a bivalent agonist of the present invention have affinity. Such cells include, but are not limited to, cells of any or tissue type, including human, mammalian, murine, canine, feline, equine, bovine, porcine, etc.

The ligand domains of the bivalent agonists are bonded covalently to a molecular backbone that renders the bivalent agonists flexible. enough to allow both ligand domains thereof to bind to two GPCRs of a desired cell type, and soluble in aqueous or physiological systems. By "backbone" is meant any biocompatible molecule functioning as a means to link the two ligand domains. Each ligand domain is linked to the molecular backbone via a covalent bond, preferably via an amide or peptide bond between an amino group of the backbone and a carboxyl group, or its equivalent, of the ligand domain, or vice versa. By "flexible" is meant that the backbone comprises a plurality of carbon-carbon a bonds having free rotation about their axes, so as to allow the two agonist or two antagonist ligand domains bonded thereto to be separated by a distance ranging from about 40 to about 250 Å, preferably from about 40 to about 150 Å.

Suitable backbones comprise group(s) such as, but are not limited to, proteins; polynucleotides; saccharides including monosaccharides, oligosaccharides, cyclodextrins and dextran; polymers including polyethylene glycol, polypropylene glycol, polyvinyl alcohol, hydrocarbons, polyacrylates and amino-, hydroxy-, thio- or carboxy-functionalized silicones; other biocompatible material units; and combinations thereof. However, due to solubility and flexibility limitations, the backbone should not be solely polyglycine or polyproline. In addition, in a preferred embodiment, the backbone cannot be an antibody. Such backbone materials described above are widely commercially available or obtainable via synthetic organic methods commonly known to those skilled in the art.

It should be noted that proteins as described herein can comprise, and amino acids as used herein refer not only to "natural," i.e., naturally occurring amino acids, but also to "non-classical," D-amino acids including, but not limited to, the D-isomers of the common amino acids, α-isobutyric acid, 4-aminobutyric acid, hydroxyproline, sarcosine, citrulline, cysteic acid, t-butylglycine, t-butylalanine, phenylglycine, cyclohexylalanine, β-alanine, designer amino acids such as β-methylamino acids, Cα-methyl amino acids, Nα-methyl amino acids, and amino acid analogs in general. In addition, the amino acids can include Abu, 2-aminobutyric acid; γ-Abu, 4-aminobutyric acid; ε-Ahx, 6-aminohexanoic acid; Aib, 2-aminoisobutyric acid; β-Ala, 3-aminopropionic acid; Orn, ornithine; Hyp, trans-hydroxyproline; Nle, Norleucine; Nva, norvaline.

By "combinations thereof" is meant that the backbones can comprise more than one class of the groups described above, e.g., can comprise saccharide and hydrocarbon groups; peptide, hydrocarbon and silicone groups; and the like; as well as being able to comprise more than one member within a class. Where the backbone comprises more than one class of group, such backbones are preferably obtained by joining different units via their functional groups. For example, in the case of a backbone comprising a saccharide and a nucleophilic group-bearing unit such as polyethylene glycol, polypropylene glycol, polyvinyl alcohol, silicone, or a peptide comprising serine or tyrosine, the hydroxyl group-bearing groups can form stable glycosidic bonds with the glycoside terminus of a saccharide. Methods for forming such bonds involve standard organic synthesis and are well known to those of ordinary skill in the art.

The molecular backbone can optionally comprise nucleophilic or electrophilic functional groups which can form ionic or covalent bonds with other species such as pharmaceutical agents, i.e., drugs, or synthetic gene therapy vectors, so as to provide a means to allow these species to be endocytosed by a cell having G-coupled protein receptors. Synthetic gene therapy vectors include non-viral vectors or other expression constructs, that preferably target a vector to a specific cell type. Examples of suitable nucleophilic groups include amino, hydroxyl and sulfhydryl groups. Examples of suitable electrophilic groups include carboxyl groups and their equivalents, and epoxide groups. It is to be understood that groups that are considered equivalent to carboxyl groups include esters, acid halides, carboxylates, and the like.

Where the other species forms ionic bonds with the functional groups of the molecular backbone, the backbone can comprise amino groups, and the other species can comprise carboxyl groups, so as to form a stable salt complex. Conversely, the molecular backbone can comprise carboxyl groups and the other species, amino groups.

Where the other species forms covalent bonds with the functional groups of the molecular backbone, the backbone can comprise amino, hydroxyl or sulfhydryl groups which can form amide, ester or thioester bonds, respectively, with a carboxyl group, or its equivalent, of the other species, and vice versa. Similarly, epoxide-functionalized backbones can form stable adducts with free amino, hydroxyl or sulfhydryl groups of the other species, and vice versa.

For example, in an embodiment wherein a drug or vector is to be bonded to the backbone, a pendant amino group of the backbone can comprise an electrophilic group, such as for example a carboxyl group or its equivalent, capable of forming a covalent, i.e., an amide, bond with the amino group. In another example, the drug or the vector to be bonded to the a pendant amino group can contain a carboxylic acid group, capable of forming an ionic bond, i.e., a salt, with the amino group, so as to form an ammonium group therewith. It is to be understood that the backbone can comprise both charged and uncharged functional groups, such that the charged functional groups can be available for ionically bonding to the other species, whereas the uncharged functional groups can be available for covalently bonding to the other species.

In addition, the backbones can comprise charged functional groups, such as for example, ammonium groups or carboxylate groups. The charged functional groups can provide bivalent agonists with sufficient solubility in aqueous or physiological systems, provide reactive sites for ionic bonding with other species, and enhance their avidity to GPCRs. Such ammonium groups can be formed via reaction between an amino group of a backbone, and acid including, but not limited to hydrochloric, acetic, citric, malic, succinic, tartaric salts, and the like. Such carboxylate groups can be formed via reaction between a carboxyl group of a backbone, and a base such as an alkali metal carbonate or bicarbonate. It is within the purview of one of skill in the art to select a particular acid, and concentration thereof, to confer optimal solubility and avidity properties to the bivalent agonists. Preferably, the total amount of charged functional groups are minimized so as to maximize the bivalent agonists'specificity for GPCRs, but not so as to significantly decrease solubility or eliminate the potential carrier function, i.e., ionic or covalent bond formation, of the charged functional groups.

If both the ligand domain and the backbone comprise an amino acid such that an amino acid of the ligand domain and an amino acid of the backbone form a peptide bond linking the ligand domain to the backbone, such a peptide bond can be formed from either the N-terminal of the ligand domain amino acid and the C-terminal of the backbone amino acid, or vice versa.

The ligand domains are situated on the backbone such that the distance between them is sufficient to allow the ligand domains of the bivalent agonists to bind to two adjacent GPCR molecules of a cell. Preferably, the distance between the ligand domains ranges from about 40 to about 250 Å, or from about 40 to about 150 Å, or from about 40 to about 125 Å, more preferably from about 60 to about 120 Å, and most preferably from about 80 to about 100 Å. While the ligand domains can be situated anywhere on the backbone as long as the distance between them ranges from about 40 to about 250 Å, each ligand domains is preferably located at each terminal end of a linear backbone.

It is to be understood that the distance of about 40 to about 250 Å is that distance which separates two adjacent GPCR molecules. Because the backbone of the bivalent agonist is flexible, the bivalent agonist is capable of assuming a conformation that allows the ligand domains thereof to bind to adjacent GPCRs. Thus, for complete and effective binding of the bivalent agonist ligand domains to a GPCR, the ligand domains should be able to assume a distance of about 40 to about 250 Å therebetween. Such a distance can be measured, or predicted theoretically, by any method known in the art. For example, molecular modeling can be used to determine distances between ligand domains in bivalent agonists of the invention, based upon, e.g., the predicted conformation of the molecule. Molecular modeling programs that can be used are commonly known and available in the art. In an alternative embodiment, the distance between ligand domains is measured by reacting a bivalent agonist, preferably a bivalent agonist having amino functional groups, with a reactive species, such as for example a halogen-substituted benzoyl halide, known to convert a non-crystalline species to a crystalline species. Such a crystalline species can be subjected to x-ray diffraction, such that the distance between its ligand domains can be determined.

5.2 Peptide Dimers

In a specific embodiment, the bivalent agonists are peptide dimers. By "peptide dimer" is meant that the two ligand domains and the molecular backbone of the bivalent agonists of the present invention each comprises one or more peptides. Like all of the bivalent agonists of the invention, peptide dimers are capable of binding to two receptor molecules simultaneously. While not being bound to any particular theory, it is the inventors' belief that binding to two receptor sites simultaneously results in a dramatic increase in agonist activity, whether the ligand domains recognize the same or different receptors.

The present peptide dimers preferably comprise two ligand domains each covalently linked to the ends of a backbone; the backbone comprising two spacer regions, two polylysine regions, and a disulfide bond region. It is to be understood that the peptide dimers can be heterodimers, wherein each ligand domain, spacer region, polylysine region or disulfide bond region is non-identical; or that the peptide dimers can be homodimers, wherein each ligand domain, spacer region, polylysine region and disulfide bond region is identical.

The ligand domains of the peptide dimers facilitate binding between the peptide dimers and GPCRs of a desired cell type. Useful ligand domains are those described above for bivalent agonists in general. Preferably, the ligand domains of the peptide dimers comprise α-MSH, α-MSH-ANT or bombesin.

As described above for the bivalent agonists, the peptide dimers comprise a backbone to which the ligand domains are covalently bonded. In the case of the preferred peptide dimers, the backbone comprises two spacer regions, two polylysine regions, and a disulfide bond region, the ligand domains, spacer regions, polylysine regions and disulfide bond region being bonded covalently together in the order: (ligand domain)-(spacer region)-(polylysine region)-(disulfide bond region)-(polylysine region)-(spacer region)-(ligand domain).

The spacer regions of the backbone of the peptide dimers allow the peptide dimers to bind to two receptor sites simultaneously. To accomplish this, the spacer region must be long enough to span two receptors, but flexible enough to permit binding to a second receptor site. In other words, suitable spacer regions are those that can assume a stable, extended secondary structure configuration, while remaining flexible and sufficiently soluble in aqueous or physiological systems. Such spacer regions include proteins; polyethylene or propylene glycols being terminated at one end with a carboxyl group; hydrocarbons being terminated at each end independently with a sulfhydryl, hydroxyl, amino or carboxyl group; and combinations thereof. However, due to solubility and flexibility limitations, the spacer region cannot be polyglycine or polyproline. Preferably, the spacer region comprises an amino acid or a di-, tri- or tetrapeptide, that forms a thioester, ester or amide bond with a terminal sulfhydryl, hydroxyl or amino group, respectively, of a hydrocarbon that is terminated at the other end with a carboxyl group. Most preferably, the spacer region is GGG-εAhx. Such spacer regions are available commercially, or can be prepared according to conventional organic synthetic techniques.

While not required, the spacer regions are preferably the part of the backbone that connects the backbone to the ligand domains, such that the ligand domains are linked to the backbone via the spacer regions of the backbone. Preferably, the bond between the ligand domains and the spacer regions is a peptide bond.

The polylysine regions of the backbone of the peptide dimers can be charged to provide the dimers with sufficient solubility in aqueous or physiological systems, provide reactive sites for ionic bonding with other species and enhance their avidity to GPCRs. By "charged" is meant that at least one of the pendant amino groups of a lysine repeat unit of one of the polylysine regions bears a positive charge, such that the charged amino group is in the form of an acid salt. Such acid salts of amino groups of lysine repeat units include, but are not limited to hydrochloride, acetate, citrate, malate, succinate, tartrate salts, and the like. It is to be understood that the polylysine regions should bear sufficient charge such that the peptide dimers remain soluble in aqueous or physiological systems. In a preferred embodiment, at least one of the amino groups of a polylysine region of a bivalent agonist of the present invention bears a positive charge.

The polylysine regions are preferably greater in length (Å) than the spacer regions, and range from about 5 to about 30 lysine repeat units. Preferably, the polylysine regions are 20 repeat units in length.

The polylysine regions bear pendant amino groups or if they are charged, ammonium groups, that are capable of forming, in the case of amino groups, covalent bonds, and in the case of ammonium groups, ionic bonds, with other species. Such "other species" include, for example, pharmaceutical agents and synthetic gene therapy vectors.

While not required, the polylysine regions are preferably the part of the backbone that connects the spacer regions to the disulfide bond region, discussed below. It is preferable that the bond formed between the polylysine regions and the disulfide bond region is a peptide bond.

The present peptide dimers comprise a disulfide bond region. The disulfide bond region provides a convenient means for linking the end of the two polylysine regions that are not bonded to the spacer domains.

The disulfide bond region includes proteins, such as peptides (with the proviso that the proteins are not polyglycine or polyproline); polyethylene or propylene glycols being terminated at one end with a carboxyl group; hydrocarbons being terminated at each end independently with a sulfhydryl, hydroxyl, amino or carboxyl group; and combinations thereof, each having at least one disulfide bond. Preferably, the disulfide region comprises two cysteine residues linked via their sulfhydryl groups, so as to contain a disulfide bond. In a specific embodiment, the disulfide region is two cysteine residues linked via their sulfhydryl groups, and capped at either their N- or C-terminus with β-alanine.

The disulfide bond of the disulfide bond region is preferably formed via oxidation, according to the procedure of Mills Jr. et al., *J. Am. Chem. Soc.* 62, 1173 (1940), or by any other procedure known to those skilled in the art useful for dimerizing a sulfhydryl-bearing moiety, of a sulfhydryl group of a corresponding monomer. Preferably, the disulfide bond is formed via oxidation of the monomer sulfhydryl group using DMSO according to the procedure of J. P. Tam et al., *J. Am. Chem. Soc.* 113, 6657–6662 (1991). Most preferably, the sulfhydryl group is of a cysteine residue covalently bonded to one end of the polylysine region of the monomer. In this case, the cysteine residue forms a covalent bond with the amino- or carboxy-terminus of the polylysine region not bonded to the spacer region.

In a specific embodiment, peptide dimers are prepared from solid phase synthesis of monomers followed by oxidative dimerization of a terminal cysteine sulfhydryl group.

Illustrative peptide dimers of the present invention have the following structures:

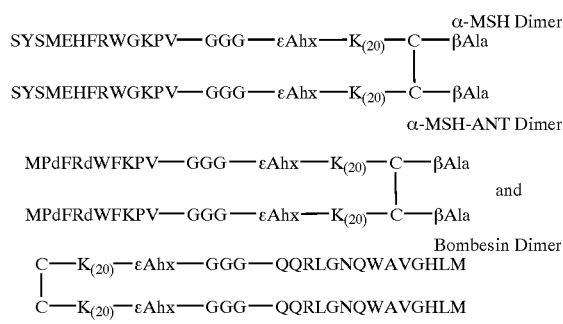

With regard to the illustrative peptide dimers, above, the ligand domains of the α-MSH dimer have the structure SYSMEHFRWGKPV-(SEQ ID NO:1); the ligand domains of the α-MSH-ANT dimer have the structure MPdFRdWFKPV-; and the ligand domains of the bombesin dimer have the structure MLHGVAWQNGLRQQ-(SEQ ID NO:2). The spacer regions of the α-MSH, α-MSH-ANT and bombesin peptide dimers are GGG-εAhx. The polylysine regions of the α-MSH, α-MSH-ANT and bombesin peptide dimers are a polypeptide of 20 lysine units ($K_{(20)}$). The disulfide bond region of the α-MSH and α-MSH-ANT dimers is two cysteine residues linked via a disulfide bond formed from their sulfhydryl groups, and end capped at their C-termini with β-alanine. The disulfide bond region of the bombesin dimer is two cysteine residues linked via a disulfide bond formed from their sulfhydryl groups. It is to be pointed out that the terminal ends of the α-MSH and the α-MSH-ANT dimer are amino-terminated, and the terminal ends of the bombesin dimer are carboxy-terminated.

It is to be pointed out that while the invention is not limited to homodimers, i.e., dimers that are symmetric with respect to their disulfide bond, the present preferred peptide dimers are homodimers. Thus, the present invention encompasses peptide dimers that are heterodimers. Such heterodimers can be synthesized from, for example, two cysteine moieties having a disulfide bond therebetween, and synthesized by oxidatively dimerizing cysteine with DMSO according to the procedure of J. P. Tam et al., *J. Am. Chem.*

Soc. 113, 6657–6662 (1991). This substrate can be protected with common protecting groups for peptides, such as those described in T. W. Greene, *Protective Groups in Organic Synthesis*, John Wiley & Sons, New York (1981), and used to synthesize, via conventional solid-phase methods, polylysine regions, spacer regions and ligand domains that differ from one end of the dimerized cysteine substrate to the other. Following this approach, heterodimers can be easily made.

5.3 Monomers Useful for Synthesing Peptide Dimers

The preferred peptide dimers are conveniently and preferably prepared from oxidative dimerization of monomers. Such monomers comprise a ligand domain covalently bonded to a molecular backbone, the ligand domain (a) being an agonist for a GPCR, and (b) comprising a peptide; the backbone comprising a spacer region, a polylysine region, all as described above in Section 5.2 for peptide dimers, and a sulfhydryl group region. Preferably, the sulfhydryl group region is the amino acid cysteine, linked to the polylysine region via a peptide bond. It is to be understood that the term "monomer" as used in this context refers to a monovalent agonist or antagonist, having a ligand domain that is an agonist, or antagonist, respectively, for a GPCR, and which is useful as an intermediate in making the present peptide dimers, whose ligand domain and backbone comprise peptides.

The monomers are synthesized by joining, in any feasible order, the ligand domain, the spacer region, the polylysine region and the sulfhydryl group region, preferably as a moiety of cysteine, such that the monomer is arranged in a (ligand domain)-(spacer region)-(polylysine region)-(sulfhydryl group region) array in covalent linkage. In the case where the sulfhydryl group region is cysteine, the monomer will have the structure: (ligand domain)-(spacer region)-(polylysine region)-(cysteine). Thus in a preferred embodiment, the sulfhydryl group region is an amino acid residue containing a sulfhydryl group. In a specific embodiment, the monomers comprise proteins and are synthesized using conventional solid phase methods. Where solid phase synthesis is used to prepare the monomers, the monomers can be prepared such that the ligand domain thereof is situated at the amino terminus of the polypeptide, or synthesized in the opposite direction such that the ligand domain is located at the carboxyl end.

The monomers are oxidized, preferably using DMSO, to afford the peptide dimers, via oxidative dimerization. In this fashion, the resulting peptide dimers are symmetrical with respect to the disulfide bond thereof, such that each of its ligand domains, spacer regions and polylysine regions are identical. In other words, the resulting peptide dimers are homodimers.

The oxidative dimerization comprises treating an amount of a monomer with an amount of an oxidizing agent capable of oxidizing its sulfhydryl group, such that an oxidized sulfhydryl group reacts with an unoxidized sulfhydryl group of another monomer so as to form a peptide dimer having a disulfide bond. In a preferred embodiment, the amount of monomer is about 2 equivalents, and the amount of oxidizing agent is about 1 equivalent.

5.4 Compositions Comprising Bivalent Agonists and Methods of Treatment Employing such Compositions The bivalent agonists of the invention are useful for activating adjacent receptors specific for that bivalent agonist, so as to elicit an appropriate second messenger response. In other words, the bivalent agonists bind to their corresponding adjacent GPCRs so as to initiate a desired physiological response. It is believed that where the bivalent agonists comprise two ligand domains which by themselves are agonists to a different GPCR, such a physiological response will occur with synergistic efficacy relative to the sum of two agonists individually. Where the bivalent agonists comprise two ligand domains which by themselves are antagonists, it is believed that the bivalent agonist will agonize the corresponding GPCRs, rather than antagonize them in the manner they would had the antagonist ligand domains been administered individually. In addition, where the bivalent agonists comprise one agonist ligand domain and one antagonist ligand domain it is believed that the bivalent agonist will behave as an agonist.

For example, if it is desired clinically to raise the systolic and/or diastolic blood pressure of a patient or subject, a practitioner can administer a bivalent agonist of the invention having two angiotensin II ligand domains, a bivalent agonist having two ligand domains which are by themselves angiotensin antagonists, such as $(Sar^1,Ile^8)$-angiotensin II, or alternatively, a bivalent agonist that has one angiotensin II ligand domain and the $(Sar^1,Ile^8)$-angiotensin II antagonist ligand domain. Similarly, if it is desired to systemically increase the levels of luteinizing hormone, a practitioner can administer a bivalent agonist of the invention having two LH-RH ligand domains, a bivalent agonist having two ligand domains which are by themselves LH-RH antagonists, such as $(D-Phe^2,D-Ala6)$-LH-RH, or alternatively, a bivalent agonist that has one LH-RH ligand domain and one $(D-Phe^2,D-Ala^6)$-LH-RH ligand domain. By way of another example, a bivalent agonist, with ligand domains that are both α-MSH agonists, can be used to promote skin tanning.

Thus, the invention provides methods of treatment by administration of a human or veterinary patient or subject of an effective amount of a bivalent agonist according to the invention. In one embodiment, the bivalent agonist is a peptide dimer, described in Section 5.2, above.

Various delivery systems are known and can be used to administer the bivalent agonists of the invention, e.g, aqueous solution, encapsulation in liposomes, microparticles, microcapsules, receptor-mediated endocytosis (see, e.g., Wu and Wu, 1987, *J. Biol. Chem.* 262, 4429–4432). Methods of administration include but are not limited to direct application to the skin, intradermal, intramuscular, intravenous, intranasal, epidural and oral routes. The bivalent agonists of the invention may be administered by any convenient route, for example, by infusion or bolus injection, by absorption through epithelial or mucocutaneous linings (e.g., oral mucosa, rectal and intestinal mucosa).

In a specific embodiment, it may be desirable to administer the bivalent agonists according to the invention locally to the area it is desired to treat by any of the above described methods.

The present invention also provides pharmaceutical compositions. Such compositions, useful for agonizing one or more GPCR, comprise a therapeutically effective amount of a bivalent agonist of to the invention, and a pharmaceutically acceptable carrier or excipient. Such a carrier includes but is not limited to water, saline solution, e.g., physiological saline, buffered saline, dextrose, glycerol, ethanol, and combinations thereof. Such a bivalent agonist formulation should suit the method of administration.

The composition, if desired, can also contain minor amounts of wetting or emulsifying agents, or pH buffering agents. The composition can be a liquid solution, suspension, emulsion, tablet, pill, capsule, sustained release formulation, cream, gel or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate.

In a specific embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the compositions are administered by injection, an ampoule of sterile water for injection or saline can be provided so that the ingredients may be mixed prior to administration.

As mentioned in Section 5.1, above, the backbones of the bivalent agonists can comprise nucleophilic or electrophilic functional groups, including amino and carboxyl groups. Accordingly, the bivalent agonists of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the bivalent agonist of the invention which will be effective in the treatment of a particular disorder or cosmetic condition will depend on the nature of the disorder or condition, which can be determined by standard clinical techniques. In addition, in vitro or in vivo assays may optionally be employed to help identify optimal dosage ranges. The precise dose to be employed in the formulation will also depend on the route of administration, and the seriousness or advancement of the disease or cosmetic condition, and should be decided according to the judgment of the practitioner and each patient's circumstances. Effective doses may be extrapolated from dose-response curves derived from in vitro or animal model test systems as provided herein.

An effective amount of the bivalent agonists is readily determined by administering graded doses of bivalent agonists according to the invention and observing the desired effect. The data provided in FIGS. 3–7, infra, will assist in determining the effective amounts.

In one embodiment, the effective concentration for an illustrative peptide dimer α-MSH-ANT in a topical formulation for, e.g., skin tanning agents, is in the range of 1 µM through 10 mM, preferably 100 µM through 5 mM, and most preferably 500 µM through 2 mM. In a particular embodiment, the effective concentration for a topical formulation is about 1 mM.

In another embodiment, an effective dose of a bivalent agonist for systemic administration for, e.g., the tanning of skin, is in the range of 1 through 4000 µmol/kg of body weight, preferably 20 through 200 µmol/kg of body weight, and most preferably 30 through 100 µmol/kg of body weight. In another embodiment, the effective dose is in the range of 30 through 100 µmol/kg of body weight.

The effective concentrations and doses for illustrative α-MSH-peptide and bombesin peptide dimers may, for example, be readily determined by reference to FIGS. 3–7.

In another alternative embodiment, the invention comprises kits containing an effective amount of a bivalent agonist according to the invention. Thus, the kit is contemplated to comprise one or more containers containing at least one bivalent agonist according to the invention. Simply by way of example, the kit will contain a bivalent agonist, or combinations of bivalent agonists formulated for application to the skin, or for administration by intradermal, intramuscular, intravenous, intranasal, epidural and oral routes of administration. The kits may contain a liquid solution, suspension, emulsion, tablet, pill, capsule, sustained release formulation, cream, gel or powder form of the bivalent agonist in premixed form or as separate ingredients ready to be mixed or formulated into a peptide formulation or a pharmaceutical composition, comprising an effective amount of the bivalent agonist according to the invention.

The following series of examples are presented by way of illustration and not by way of limitation on the scope of the invention.

6. EXAMPLE

Synthesis and Characterization of Bivalent Peptide Ligands Targeted to G-Protein Coupled Receptors Through the effects of avidity, bivalency can increase the apparent affinity of a ligand for its binding site. High affinity, bivalent agonists, such as peptide dimers, can be used to deliver a variety of agents to specific cell subtypes having GPCRs. In order to target these GPCRs, a series of peptide dimers were synthesized so as to bind to adjacent receptor sites. Such peptide dimers comprise two ligand domains, two spacer region, two polylysine regions and a disulfide bond region, such that the order in which the ligand domains, spacer regions, polylysine regions and disulfide bond region are bonded together is: (ligand domain)-(spacer region)-(polylysine region)-(disulfide bond region)-(polylysine region)-(spacer region)-(ligand domain).

6.1 Materials and Methods

Materials. Fmoc-Ala-OH, Fmoc-Arg(Pmc)-OH, Fmoc-Asn(Trt)-OH, Fmoc-Asp(O-tBu)-OH, Fmoc-Gln(Trt)-OH, Fmoc-Glu(O-tBu)-OH, Fmoc-Gly-OH, Fmoc-His(Trt)-OH, Fmoc-Ile-OH, Fmoc-Leu-OH, Fmoc, Lys(Boc)-OH, Fmoc-Met-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, Fmoc-Val-OH, HBTU, HOBt, MBHA resin, and Rink amide MBHA resin were obtained commercially from Calbiochem-Nova Biochem, La Jolla, Calif.; dichloromethane, DMF, DIEA, NMP and TFA were obtained from Applied Biosystems, Foster City, Calif.; ethanol, methanol, pyridine, potassium cyanide, ninhydrin and phenol were obtained from Aldrich Chemical Co., Milwaukee, Wis.

Peptide Synthesis. Peptide synthesis, analytical HPLC, laser desorption mass spectroscopy and amino acid analysis were performed at the W.M. Keck Foundation Resource Laboratory of Yale University. Peptides were synthesized by solid phase on a Rainin Symphony Multiple Peptide Synthesizer using Fmoc protecting group chemistry. Following cleavage from the rink amide MBHA resin by TFA, peptides were analyzed by reverse phase HPLC (Vydec $C_{18}$ column) and mass spectroscopy.

Example 1

0.45 M HBTU/HOBt Reagent in DMF. 50 mL of 0.5 M (DMF) HOBt was poured into a 125 mL amber bottle containing 25 mmol of dry HBTU. The HBTU was dissolved with gentle swirling. The final concentration of the HBTU and HOBt was 0.45 M. The resulting solution was stable at room temperature for at least six weeks.

Example 2

Synthesis of Monomers. All Fmoc-amino acids were coupled to the MBHA linker as follows: 1 mmol of derivatized amino acid was dissolved in 2.5 mL of NMP, 2.0 mL of the 0.45 M HBTU/HOBt reagent in DMF obtained according to the procedure of Example 1 was added to the amino acid solution, and the resulting solution was mixed for 10 min. and transferred to the MBHA resin. 2.0 mL of DIEA was added to the resin suspension, and incubated at room temperature for 30 min. while mixing. The resulting amino acid-coupled resin was filtered and rinsed six times with NMP, and 2 mg of beads were removed for quantitative ninhydrin testing. The amino acid-coupled resin was deprotected by a 5 min. treatment, followed by an additional 15 min. treatment, with 20% piperidine/NMP. The resulting deprotected amino acid-coupled resin was filtered, rinsed six times with NMP, and used in successive iterations of the above process until the peptide sequence for the desired monomer was achieved.

Example 3

Cleavage of Monomers from MBHA Resin. After the desired monomer was synthesized, the monomer was cleaved from the MBHA resin by exposing the resin to gaseous TFA for 0, 2, 4, 6 and 10 h. Cleavage was quantified by HPLC analysis.

Example 4

Oxidation of Monomers to Peptide Dimers. Following cleavage of the monomers from the MBHA resin according to the procedure of Example 3, the resulting monomers oxidized according to the procedure of J. P. Tam et al., *J. Am. Chem. Soc.* 113, 6657–6662 (1991). Thus, the resulting monomers were extracted with 25% acetic acid, followed by a second extraction with 5% acetic acid. Combined acetic acid washings were diluted to a final concentration of 5% acetic acid, and the resulting monomer solution was adjusted to pH 6 using $(NH_4)_2CO_3$. DMSO at 20% by volume was added, and after 1–4 h, the analogous peptide dimers were obtained.

HPLC. HPLC purification of peptides was performed on a Pharmacia SMART system using Superdex Peptide and Superose 6 size exclusion columns. Following synthesis, peptides were purified on a Superdex Peptide column in PBS at a flow rate of 50 uL/min and used immediately for oxidation reactions. Following oxidation, monomers and dimers were repurified on a Superose 6 column in PBS at a flow rate of 50 uL/min. Dimers usually required two successive gel filtration steps to achieve suitable purity. Peptides were stored in PBS at −200 C. The concentration of the peptides was determined by amino acid analysis, and molecular weights were confirmed by mass spectroscopy.

Oxidation. After peptides were purified on a Superdex Peptide column, they were oxidized at room temperature for 4 hrs in PBS (pH=7.0) containing 20% dimethylsulfoxide (DMSO) (J. P. Tam et al., *J. Am. Chem. Soc.* 113, 6657–6662 (1991)). The average yield for the dimeric peptides was approximately 20%.

Frog Melanocyte Assay. Xenopus laevis melanophores were maintained in culture as described by M. Engel et al., *Biochemistry* 30, 3161–3169 (1991); C. A. Slate et al., *Int. J. Peptide Protein Res.* 45, 290–298 (1995); and C. Plank et al., *J. Biol. Chem.* 269, 12918–12924 (1994). Transient expression of bombesin receptor plasmid DNA (pJG3.6BR) in melanophores was achieved by electroporation (C. A. Slate et al., *Int. J. Peptide Protein Res.* 45, 290–298 (1995)). Melanophores were plated (15,000 per well) on 96 well tissue culture plates (Falcon), and time and dose-response curves were obtained by microtiter plate assays (R. Duncan et al., *Clin. Pharmacokinet.* 27, 290–306 (1994); M. Engel et al., *Biochemistry* 30, 3161–3169 (1991); C. A. Slate et al., *Int. J. Peptide Protein Res.* 45, 290–298 (1995); C. Plank et al., *J. Biol. Chem.* 269, 12918–12924 (1994); and P. M. Conn et al., *Endocrinology* 111, 335–337 (1982)). Prior to addition of monomers or dimers, cells were washed and then incubated for one hour with 0.7× L15 media supplemented with 1 nM melatonin. This preincubation caused the cells to aggregate their pigment and lighten. Monomers or dimers were added to the microtiter wells in 20 μl aliquots at 10 times their final concentration. For $IC_{50}$ curves, the media also was supplemented with 5 nM α-MSH.

Phototransmission was measured at 620 nm using a 340 ATTC microtiter plate reader (SLT Lab Instruments). Transmission readings were taken 1 hour following the addition of melatonin (Ti), and monomers or dimers were added immediately. Additional readings ($T_f$) were made at various time points (5–60 min). Data was curve fitted by nonlinear regression with $y=1-(T_f/T_i)$. The final data was normalized and expressed as a percentage of maximal pigment dispersion ($y_{max}$).

For this study, a rapid, functional assay for G-protein-coupled receptors in frog melanophore cells (C. K. Jayawickreme et al., *J. Biol. Chem.* 269, 29846–29854 (1994); M. N. Potenza et al., *Anal. Biochem.* 206, 315–322 (1992); G. F. Graminski et al., *J. Biol. Chem.* 268, 5957–5964 (1993); S. Karne et al., *J. Biol. Chem.* 268, 19126–19133 (1993); and C. K. Jayawickreme et al., *Proc. Natl. Acad. Sci. USA* 91, 1614–1618 (1994)) was used. In frog melanocyte cells, ligands like α-MSH that mediate increases in cellular cyclic AMP levels, or like endothelin 3 that stimulate PI metabolism (S. Karne et al., *J. Biol. Chem.* 268, 19126–19133 (1993)), cause pigment dispersion and cell darkening, whereas inhibitors of cyclic AMP synthesis, like melatonin, cause pigment aggregation and cell lightening. In this study, the effect of monomeric and dimeric peptides on pigment dispersion was determined.

Wild type melanophores were used for assays involving α-MSH and α-MSH-ANT monomers and dimers. Melanophores that were transfected with a plasmid that contained the bombesin receptor coding region were used for assays involving bombesin monomer and dimer (G. F. Graminski et al., *J. Biol. Chem.* 268, 5957–5964 (1993); and C. K. Jayawickreme et al., *Proc. Natl. Acad. Sci. USA* 91, 1614–1618 (1994)).

To assess whether or not similar effects could be observed for other ligands, wild type cells were transfected (cDNA) with a plasmid encoding a bombesin receptor. The bombesin receptor is linked functionally to PI hydrolysis and has been demonstrated to mediate pigment dispersion following transfection (P. M. Conn et al., *Nature* 296, 653–654 (1982)).

6.2 Synthesis of α-MSH, α-MSH-ANT an Bombesin Monomers and Dimers

α-MSH, α-MSH-ANT and bombesin monomers were synthesized using solid phase peptide synthesis according to the procedure of Section 6.1, above. α-MSH and α-MSH-ANT dimers, whose structures are shown below, were synthesized from monomers having an N-terminal region that consisted of a ligand binding domain followed by a short, uncharged region consisting of three glycine residues and an amino-hexanoic acid spacer; a longer, charged spacer region of 20 lysine residues; and cysteine residue; and, finally, a beta-alanine residue at the carboxyl terminus. A bombesin monomer, whose structure is shown below, was synthesized in the opposite direction with the ligand binding domain at the carboxyl terminus, because, unlike the MSH monomers, the carboxyl terminus is crucial for bombesin binding. Following solid phase synthesis, the α-MSH, α-MSH-ANT and bombesin monomers were oxidized, using DMSO, to their corresponding dimers.

It is to be pointed out that the monomers used in the frog melanocyte assay described in Section 6.1 differ somewhat from the monomers used in the synthesis of the peptide dimers in these examples, in that the monomers used in such assay lack cysteine residues. This is because monomers comprising cysteine residues are susceptible to air oxidation and accordingly, are not particularly useful for obtaining baseline/control data relative to pure peptide dimers consisting of such monomers with cysteine residues. The monomers used in the studies described below have the following structures:

SYSMEHFRWGKPV-GGG-εAhx-$K_{(20)}$-βAla
α-MSH Monomer (SEQ ID NO:3)

MPdFRdWFKPV-GGGεAhx-$K_{(20)}$-βAla
α-MSH-ANT Monomer and $K_{(20)}$-εAhx-GGG-QQRLGNQWAVGHLM
Bombesin Monomer (SEQ ID NO:4)

Figure 1:
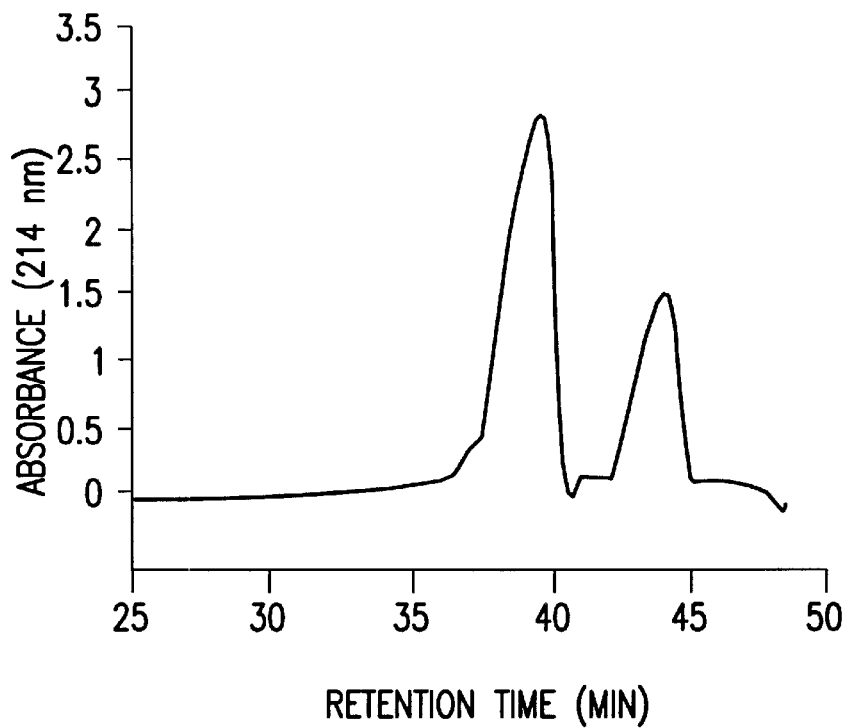
FIG. 1 is an HPLC chromatogram of an α-MSH peptide dimer of the present invention. Retention time ($R_t$)=39.0 min.
Figure 2:
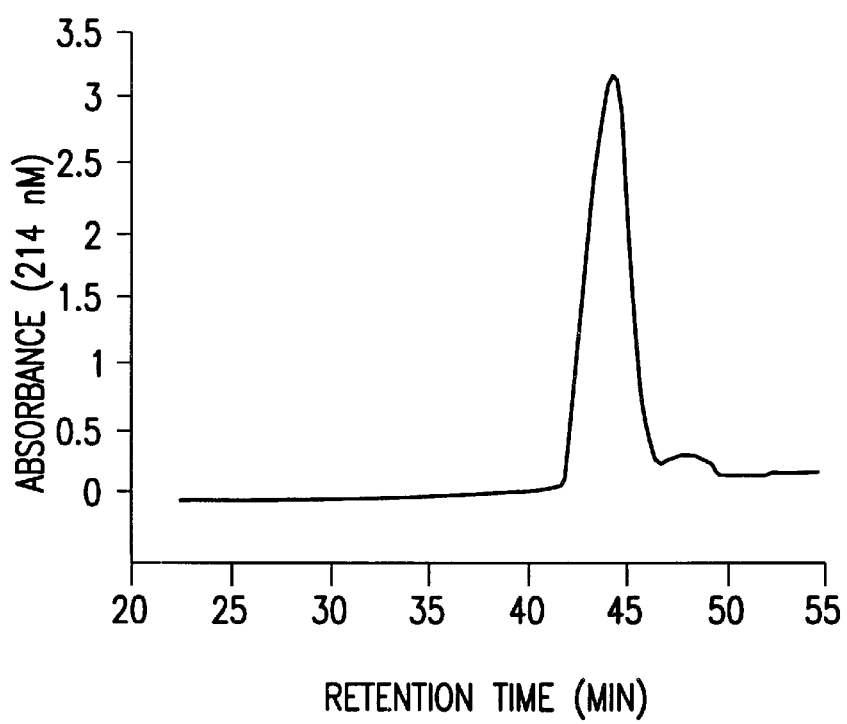
FIG. 2 is an HPLC chromatogram of an α-MSH monomer of the present invention. Retention time ($R_t$)=44.0 min.

Following HPLC purification, both cysteine and non-cysteine containing peptides were oxidized by treatment with 20% DMSO for 4 hours (J. P. Tam et al., *J. Am. Chem. Soc.* 113, 6657–6662 (1991)). Peptides then were repurified by HPLC size exclusion chromatography (Pharmacia Superose 6 column) (FIGS. 1 and 2). The dimer required two gel filtration purification steps. The approximate retention times ($R_t$) were 39.0 and 44.0 min for the dimer and the monomer, respectively. Molecular weights were confirmed by mass spectroscopy, and concentrations were determined by amino acid analysis (data not shown).

6.3 Results

Figure 3:
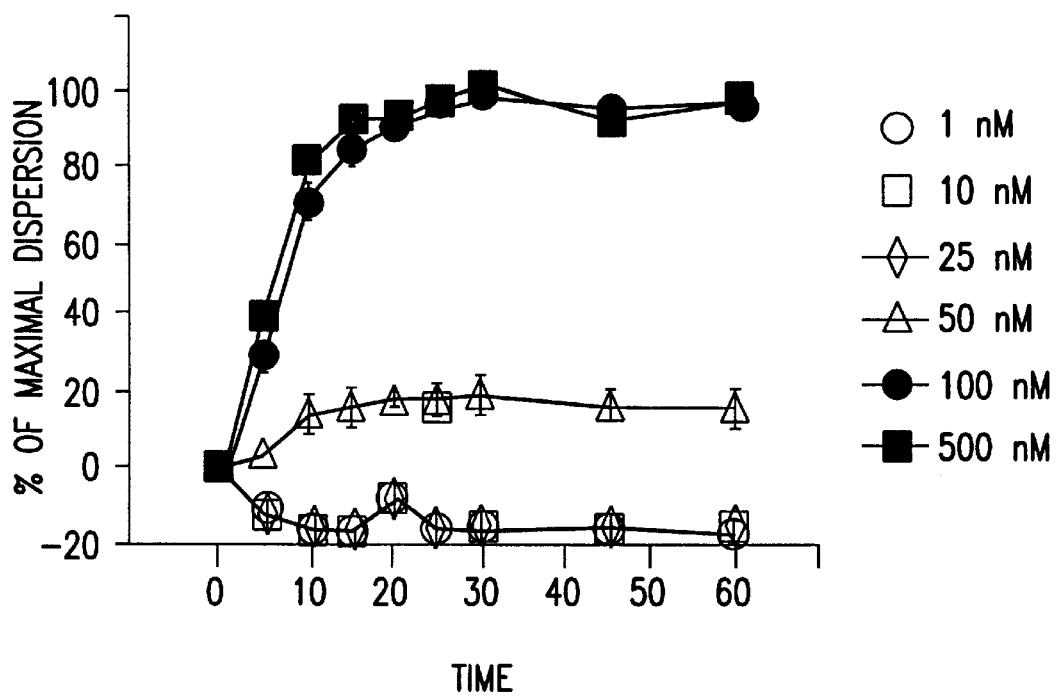
FIG. 3 is a graph showing the effect of α-MSH monomer on melanocyte pigment dispersion in a time dependent manner. Each point in the graph represents the mean from triplicate samples. ○=1 nm; □=10 nm; ◇=25 nm; △=50 nm; ●=100 nm; and ■=500 nm.

In wild type melanophores, the monomeric and dimeric α-MSH peptides stimulated dispersion in a time and dose-dependent manner (FIG. 3). However, the α-MSH dimer stimulated dispersion with an $EC_{50}$ (at t=30 min.) that was approximately 5-fold lower as compared to the monomer (FIG. 4). Calculated $EC_{50}$ values were 72.5±5.0 nM and 372±18 nM for the dimer and monomer, respectively. Thus, conversion of α-MSH monomer to its dimer resulted in a 5-fold increase in its agonist activity.

In addition, the effects of monomeric and dimeric α-MSH-ANT on pigment dispersion were examined. As expected, α-MSH-ANT monomer inhibited α-MSH (5 nM) mediated dispersion in a dose dependent manner with an $IC_{50}$=120±6 nM (FIG. 5). However, although at low concentrations α-MSH-ANT dimer appeared to inhibit α-MSH-mediated dispersion (FIG. 5), at higher concentrations α-MSH-ANT dimer predominantly stimulated dispersion (FIG. 6). No significant dispersion was observed with α-MSH-ANT monomer. The $IC_{50}$ (t=30 min) for α-MSH-ANT dimer was approximately two-fold less than that of the monomer ($IC_{50}$=57±74 nM), but it was not possible to calculate this value accurately because dispersion occurred above a concentration of 100 nM (FIG. 5). In the absence of α-MSH (FIG. 6), the calculated $EC_{50}$ for the dimer was 138±4 nM; however, above a concentration of approximately 350 nM, dimer agonism diminished. α-MSH-ANT monomer did not stimulate dispersion below a concentration of 1 μM. Above 1 μM, both peptides stimulated a small but significant degree of nonspecific pigment dispersion. Thus, conversion of α-MSH-ANT monomer to its dimer resulted in a surprising and unexpected agonist effect.

Similar to the results obtained with the α-MSH peptides as discussed above, the bombesin dimer stimulated pigment dispersion in a dose-dependent manner with an $EC_{50}$ approximately 5-fold lower than bombesin monomer (FIG. 7). The $EC_{50}$ (t=30 min) was 23.4±5.6 nM for the dimer, and 110±9 nM for the monomer. Like the α-MSH-ANT monomer, the bombesin peptides did not stimulate dispersion in wild type melanophores within the concentration range used (data not shown). Thus, conversion of bombesin monomer to its dimer resulted in an approximately 5-fold increase in agonist activity.

6.4 Conclusions

The above results demonstrate that dimeric peptides targeted to α-MSH and bombesin receptors have an affinity approximately 5-fold higher than the corresponding monomers. Since the dimers contain twice the number of potential ligands, the avidity effect was slightly more than two-fold. Although this effect was modest, it is the first demonstration to the inventors' knowledge that an entirely synthetic agonist peptide dimer can enhance G-protein mediated signaling.

Why the effect of bivalent binding to GPCRs is relatively modest may have several explanations. First, signaling may in part be regulated by α-effects of the G-protein complex and prevent excessive signal amplification. Second, models that predict an affinity increase by an order of magnitude or more assume a very high concentration of antigen or receptor on the target surface (D. M. Crothers et al., *Immunochemistry* 9, 341–357 (1972)). Third, in the case of G-protein coupled receptors, the local concentration of receptor is probably a limiting factor in affinity enhancement by multivalency.

It is also possible that the increased potency of the dimeric peptides is due to enhanced signaling through G-proteins. In prior GnRH receptor studies, it was hypothesized that microaggregation of the receptor proteins may facilitate second messenger events (P.M. Conn et al., *Endocrinology* 111, 335–337 (1982); P. M. Conn et al., *Nature* 296, 653–654 (1982)). More recent molecular studies of G-protein coupled receptors suggested that these proteins can interact and form dimers that involve the exchange of amino and carboxyl terminal domains (R. Maggio et al., *Proc. Natl. Acad. Sci. USA* 90, 3103–3107 (1993)). These dimers may activate G-proteins more efficiently than monomeric receptors.

The most important result described above was that α-MSH-ANT dimer acted as an agonist. Without being bound to any particular theory, the inventors hypothesize that the bivalent agonists mediate a cooperative effect when the two "arms" of the ligand are bound to adjacent receptors. In this scenario, receptor microaggregation or dimerization can occur and would be sufficient to stimulate a second messenger response (P. M. Conn et al., *Endocrinology* 111, 335–337 (1982); P. M. Conn et al., *Nature* 296, 653–654 (1982)).

In addition, the above results indicate that the agonism of the illustrative bivalent agonists diminished at higher concentrations. This suggests that the concentration of the receptor may become rate limiting at very high ligand concentrations (G. Fuh et al., *Science* 256, 1677–1680 (1992)). In other words, monomeric binding of ligand saturates receptor binding sites, and dimerization of receptors is inhibited.

Thus, using a functional assay in frog melanophore cells, the inventors have demonstrated that bivalent agonists having two ligand domains which act by themselves as agonists result in an increase in agonist potency relative to their corresponding monomeric forms, and that bivalent agonists that have two ligand domains which act by themselves as antagonists result in a conversion of their antagonist to agonist activity. These findings provide a potentially powerful way to target drugs to specific cell types.

The present invention is not to be limited in scope by the specific embodiments disclosed in the examples which are intended as illustrations of a number of aspects of the invention and any embodiments which are functionally equivalent are within the scope of this invention. Indeed, various modifications of the invention in addition to those shown and described herein will become apparent to those skilled in the art and are intended to fall within appended claims.

A number of references have been cited, the entire disclosures of which are incorporated herein by reference.

What is claimed is:

1. A bivalent agonist having the following structure:

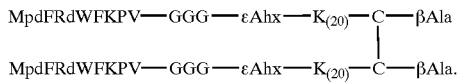

2. A composition comprising a pharmaceutically acceptable carrier and:

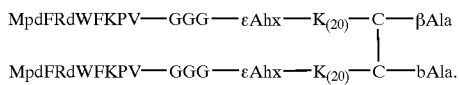

3. The composition of claim 2, wherein the bivalent agonist is purified.

4. A bivalent agonist having affinity for one or more G-protein coupled receptors, said agonist comprising two ligand domains, the ligand domains being agonists for a first and a second G-protein coupled receptor, respectively, said agonist further comprising a molecular backbone covalently bonded to the two ligand domains, the molecular backbone separating the ligand domains by a distance ranging from about 40 to about 250 Å when the agonist is unbound to a protein, wherein the backbone is not an antibody.

5. The bivalent agonist of claim 4, in which the first and the second G-protein coupled receptors are the same.

6. The bivalent agonist of claim 5, in which each ligand domain is the same.

7. The bivalent agonist of claim 4, in which the first G-protein coupled receptor is different from the second G-protein coupled receptor.

8. The bivalent agonist of claim 4, in which either the first or second G-protein coupled receptor is an MSH-receptor.

9. The bivalent agonist of claim 4, in which the first and second G-protein coupled receptors are both an MSH-receptor.

10. The bivalent agonist of claim 4, wherein the ligand domains are each independently selected from the group consisting of a hormone; an antigen; a synthetic or naturally occurring drug; an opiate; dopamine; serotonin; $Ca^{2+}$; a catecholamine; thrombin; acetylcholine; a prostaglandin; a small organic molecule that is a fragrance; a pheromone; adenosine; a simple sugar; and mixtures thereof.

11. The bivalent agonist of claim 4, wherein the backbone comprises a protein; a polynucleotide; a saccharide; polyethylene glycol; polypropylene glycol; polyvinyl alcohol; a hydrocarbon; a polyacrylate; an amino-, hydroxy-, thio- or carboxy-functionalized silicone; or a combination thereof, with the proviso that the backbone is not solely polyglycine or polyproline, and with the further proviso that the backbone is not an antibody.

12. The bivalent agonist of claim 11, wherein said backbone comprises one or more nucleophilic or electrophilic functional groups.

13. The bivalent agonist of claim 12, wherein the nucleophilic functional groups are selected from the group consisting of amino, hydroxyl and sulfhydryl groups, and the electrophilic functional groups are selected from the group consisting of carboxyl groups and their equivalents, and epoxide groups.

14. The bivalent agonist of claim 11, wherein the backbone further comprises ammonium or carboxylate groups.

15. The bivalent agonist of claim 4, wherein the two ligand domains and the backbone each comprises one or more peptides; and the backbone comprises two spacer regions, two polylysine regions and a disulfide bond region, the ligand domains, spacer regions, polylysine regions and disulfide bond region being bonded covalently together in the order: (ligand domain)-(spacer region)-(polylysine region)-(disulfide bond region)-(polylysine region)-(spacer region)-(ligand domain).

16. The bivalent agonist of claim 15, wherein the spacer regions are each independently selected from the group consisting of a protein; polyethylene or polypropylene glycol being terminated at one end with a carboxyl group; and a hydrocarbon being terminated at each end independently with a sulfhydryl, hydroxyl, amino or carboxyl group, and combinations thereof.

17. The bivalent agonist of claim 16, wherein each spacer region is GGG-εAhx.

18. The bivalent agonist of claim 15, wherein at least one of the amino groups of a polylysine region bears a positive charge.

19. The bivalent agonist of claim 15, wherein the bivalent agonist is:

20. The bivalent agonist of claim 15, wherein the bivalent agonist is:

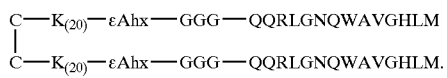

21. The bivalent agonist of claim 4, in which each ligand domain is independently selected from the group consisting of peptides, opiates, dopamine, serotonin, $Ca^{2+}$, catecholamines, acetylcholine, prostaglandins, fragrances, pheromones, adenosine, and simple sugars.

22. The bivalent agonist of claim 4, in which the distance between the two ligand domains is 40 to 250 Å.

23. The bivalent agonist of claim 22, wherein the backbone comprises a protein; a polynucleotide; a saccharide; polyethylene glycol; polypropylene glycol; polyvinyl alcohol; a hydrocarbon; a polyacrylate; an amino-, hydroxy-, thio- or carboxy-functionalized silicone; or a combination thereof, with the proviso that the backbone is not solely polyglycine or polyproline, and with the further proviso that the backbone is not an antibody.

24. The bivalent agonist of claim 4, wherein at least one of the ligand domains is thrombin.

25. A composition for agonizing one or more G-protein coupled receptors comprising an amount of the bivalent agonist of claim 4 effective for agonizing one or more G-protein coupled receptors; and a pharmaceutically acceptable carrier.

26. The composition of claim 25, wherein the bivalent agonist is purified.

27. The composition of claim 25, in which the first and the second G-protein coupled receptors are the same.

28. The composition of claim 27, in which each ligand domain is the same.

29. The composition of claim 25, in which the first G-protein coupled receptor is different from the second G-protein coupled receptor.

30. The composition of claim 25, in which either the first or second G-protein coupled receptor is an MSH-receptor.

31. The composition of claim 25, in which the first and second G-protein coupled receptors are both an MSH-receptor.

32. The composition of claim 25, wherein the ligand domains are each independently selected from the group consisting of a hormone; an antigen; a synthetic or naturally occurring drug; an opiate; dopamine; serotonin; $Ca^{2+}$; a catecholamine; thrombin; acetylcholine; a prostaglandin; a small organic molecule that is a fragrance; a pheromone; adenosine; a simple sugar; and mixtures thereof.

33. The composition of claim 25, wherein the backbone comprises a protein; a polynucleotide; a saccharide; polyethylene glycol; polypropylene glycol; polyvinyl alcohol; a hydrocarbon; a polyacrylate; an amino-, hydroxy-, thio- or carboxy-functionalized silicone; or a combination thereof, with the proviso that the backbone is not solely polyglycine or polyproline, and with the further proviso that the backbone is not an antibody.

34. The composition of claim 33, wherein said backbone comprises one or more nucleophilic or electrophilic functional groups.

35. The composition of claim 34, wherein the nucleophilic functional groups are selected from the group consisting of amino, hydroxyl and sulfhydryl groups, and the electrophilic functional groups are selected from the group consisting of carboxyl groups and their equivalents, and epoxide groups.

36. The composition of claim 33, wherein the backbone further comprises ammonium or carboxylate groups.

37. The composition of claim 25, wherein the bivalent agonist is:

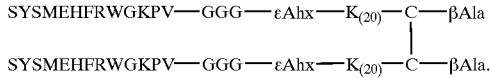

38. The composition of claim 25, wherein the bivalent agonist is:

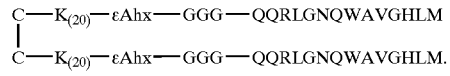

39. A method for agonizing one or more G-protein coupled receptors expressed by a cell, comprising contacting a cell with a bivalent agonist, said agonist comprising two ligand domains, the ligand domains being agonists for a first and a second G-protein coupled receptor, respectively, said agonist further comprising a molecular backbone covalently bonded to the two ligand domains, the molecular backbone separating the ligand domains by a distance ranging from about 40 to about 25 Å when the agonist is unbound to a protein, wherein the backbone is not an antibody.

40. The method of claim 39, in which the cell expresses the first or the second G-protein coupled receptor.

41. The method of claim 39, in which the cell expresses the first and the second G-protein coupled receptors.

42. The method of claim 41, in which the first and second G-protein coupled receptors are the same.

43. The method of claim 39, in which the first and second G-protein coupled receptors are different.

44. The method of claim 39, in which the first and second G-protein coupled receptors are the same.

45. The method of claim 39, in which either the first or second G-protein coupled receptor is an MSH-receptor.

46. The method of claim 39, in which the first and second G-protein coupled receptors are both an MSH-receptor.

47. The method of claim 39, wherein the ligand domains are each independently selected from the group consisting of a hormone; an antigen; a synthetic or naturally occurring drug; an opiate; dopamine; serotonin; $Ca^{2+}$; a catecholamine; thrombin; acetylcholine; a prostaglandin; a small organic molecule that is a fragrance; a pheromone; adenosine; a simple sugar; and mixtures thereof.

48. The method of claim 39, wherein the backbone comprises a protein; a polynucleotide; a saccharide; polyethylene glycol; polypropylene glycol; polyvinyl alcohol; a hydrocarbon; a polyacrylate; an amino-, hydroxy-, thio- or carboxy-functionalized silicone; or a combination thereof, with the proviso that the backbone is not solely polyglycine or polyproline, and with the further proviso that the backbone is not an antibody.

49. The method of claim 48, wherein said backbone comprises one or more nucleophilic or electrophilic functional groups.

50. The method of claim 49, wherein the nucleophilic functional groups are selected from the group consisting of amino, hydroxyl and sulfhydryl groups, and the electrophilic functional groups are selected from the group consisting of carboxyl groups and their equivalents, and epoxide groups.

51. The method of claim 48, wherein the backbone further comprises ammonium or carboxylate groups.

52. The method of claim 39, in which each ligand domain is independently selected from the group consisting of peptides, opiates, dopamine, serotonin, $Ca^{2+}$, catecholamines, acetylcholine, prostaglandins, fragrances, pheromones, adenosine, and simple sugars.

53. The method of claim 39, in which the distance between the two ligand domains is 40 to 250 Å.

54. The bivalent agonist of claim 53, wherein the backbone comprises a protein; a polynucleotide; a saccharide; polyethylene glycol; polypropylene glycol; polyvinyl alcohol; a hydrocarbon; a polyacrylat carboxy-functionalized silicone; or a combination thereof, with the proviso that the backbone is not solely polyglycine or polyproline, and with the further proviso that the backbone is not an antibody.

55. The method of claim 39, wherein at least one of the ligand domains is thrombin.

* * * * *